United States Patent
Schmidt

(10) Patent No.: US 8,116,844 B2
(45) Date of Patent: Feb. 14, 2012

(54) ANGIOGRAPHIC METHOD AND APPARATUS ALLOWING IDENTIFICATION OF CONTRAST AGENT PROPAGATION

(75) Inventor: Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 434 days.

(21) Appl. No.: 12/335,627

(22) Filed: Dec. 16, 2008

(65) Prior Publication Data

US 2009/0156927 A1 Jun. 18, 2009

(30) Foreign Application Priority Data

Dec. 17, 2007 (DE) .................. 10 2007 060 689

(51) Int. Cl.
*A61B 5/055* (2006.01)
*A61B 6/00* (2006.01)
*G01V 3/00* (2006.01)
(52) U.S. Cl. ......... 600/420; 600/431; 324/307; 324/309
(58) Field of Classification Search .................. 600/410, 600/419, 420, 431; 382/128, 130, 131; 324/307, 324/309
See application file for complete search history.

(56) References Cited

U.S. PATENT DOCUMENTS

| | | | |
|---|---|---|---|
| 6,198,960 B1 | 3/2001 | Fain et al. | |
| 6,381,486 B1 * | 4/2002 | Mistretta et al. | 600/420 |
| 7,292,720 B2 | 11/2007 | Horger et al. | |
| 2003/0169911 A1 * | 9/2003 | Snyder et al. | 382/130 |
| 2005/0177042 A1 | 8/2005 | Abe et al. | |
| 2006/0183996 A1 | 8/2006 | Abe et al. | |

OTHER PUBLICATIONS

Automated Detection of Bolus arrival and Initiation of Data Acquisition in fast, Three-dimensional, Gadolinium-enhanced MR Angiography, Foo et al., Radiology, vol. 203 (1997) pp. 275-280.

* cited by examiner

*Primary Examiner* — Michael Rozanski
(74) *Attorney, Agent, or Firm* — Schiff Hardin LLP

(57) ABSTRACT

In a method and apparatus for acquisition of angiographic data sets of a region of an examination subject, into whose bloodstream a contrast agent has been introduced, a data set of the region to be examined is acquired during a first propagation phase of the contrast agent in the bloodstream as a reference data set to determine reference data, additional data sets of the region to be examined are then acquired, and based on the reference data, variations that are caused in at least some of the additional data sets due to the arrival of a second propagation phase of the contrast agent are determined, and the arrival of the second propagation phase of the contrast agent in the bloodstream is identified based on the determined variations.

24 Claims, 5 Drawing Sheets

FIG 2
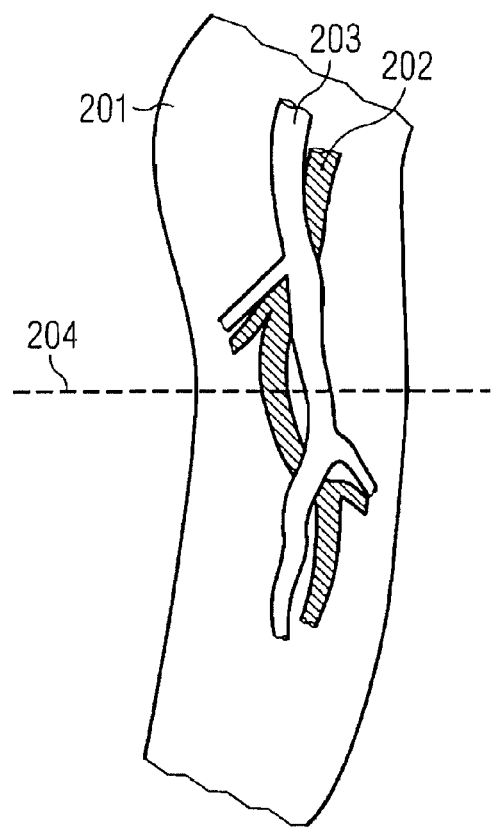
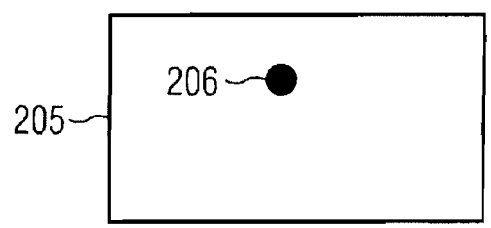
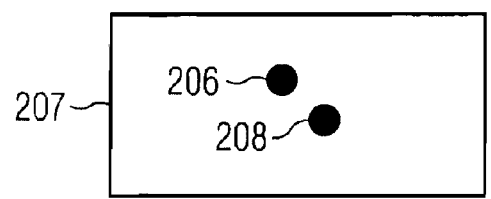

FIG 4
a)
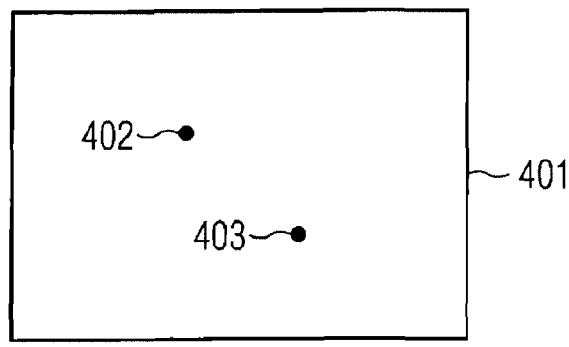
b)
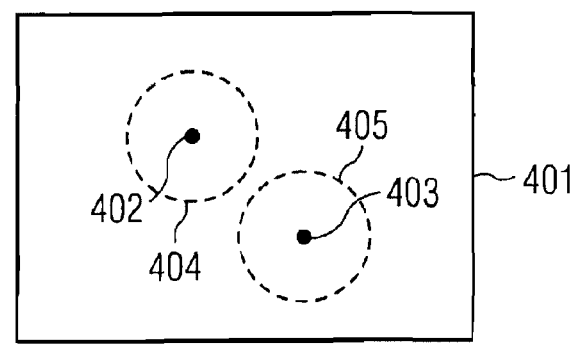
c)
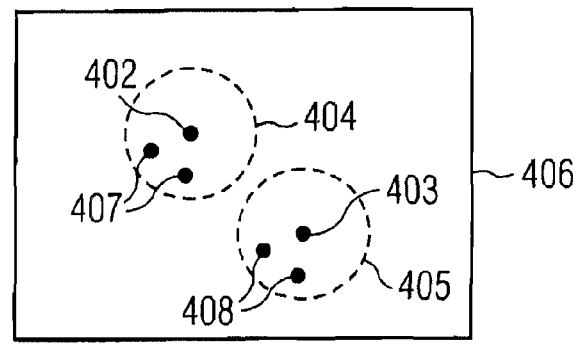

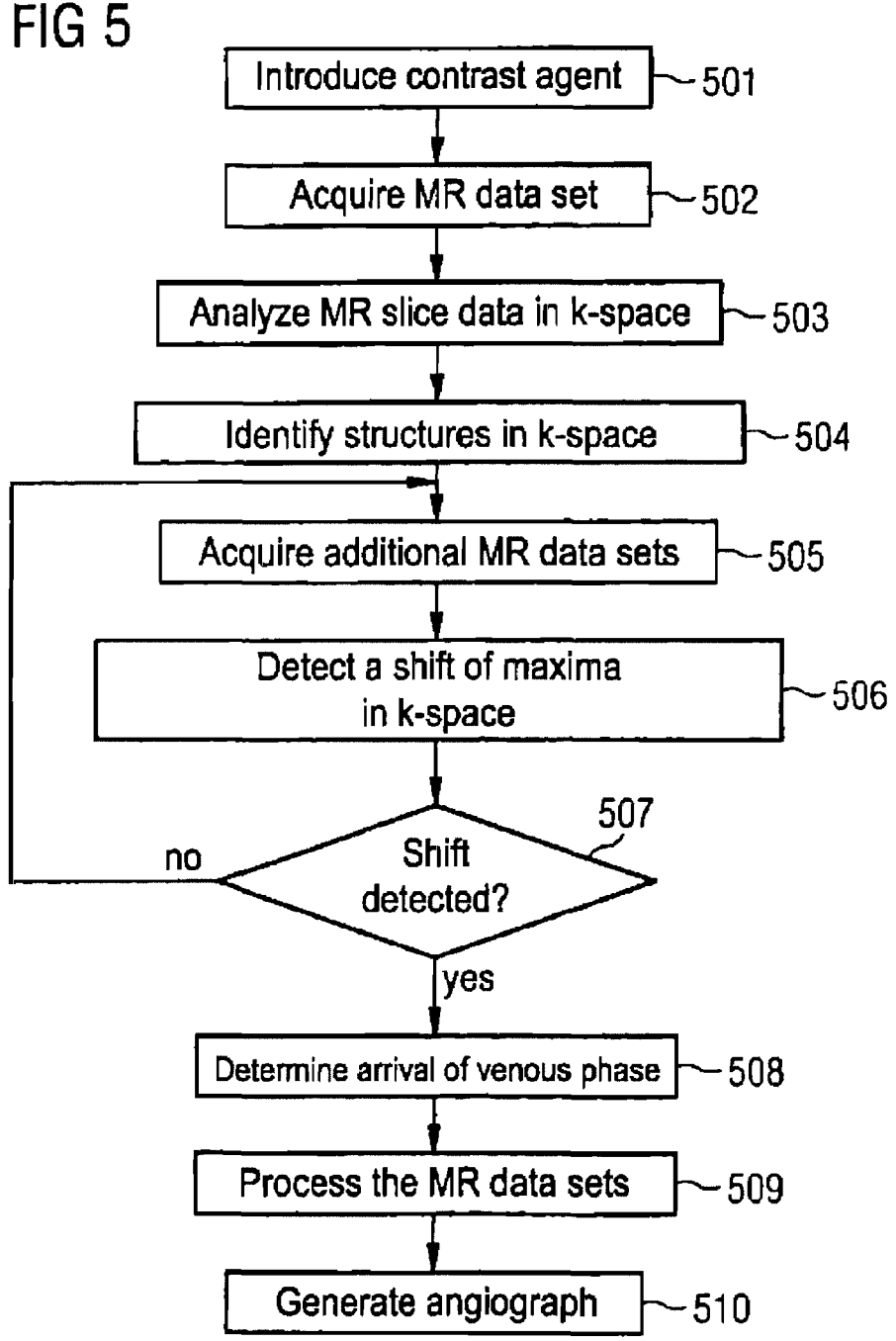

ANGIOGRAPHIC METHOD AND APPARATUS ALLOWING IDENTIFICATION OF CONTRAST AGENT PROPAGATION

BACKGROUND OF THE INVENTION

1. Field of the Invention

The present invention concerns a method for acquisition of angiographic data sets from a region of an examination subject, as well as a magnetic resonance system for acquisition of such data sets.

2. Description of the Prior Art

Angiography is a known medical diagnosis method in which blood vessels are shown by means of diagnostic imaging methods. For example, x-ray or magnetic resonance tomography methods can be used for this purpose. In magnetic resonance (MR) tomography, for example, the imaging is sensitive to the movement of nuclear spins that generate the MR signal. These effects can be used to acquire angiographic images, i.e. images of the vessels of the examined person. Angiographic techniques that are based only on the flux effects of the spins located in the body are known for this. Furthermore, contrast agent-supported MR angiography (ceMRA) is a method frequently applied in clinical practice. With this modality, primarily large vessels can be shown without ionizing radiation.

In contrast agent-based MR methods it is desirable to increase the spatial resolution, which can be achieved via longer scan times, for example. The scan times are limited, however, because the contrast agent supplied to the bloodstream of the patient passes into the tissue, so the blood/tissue contrast is reduced. This effect can be reduced by the use of blood pooling agents. Contrast agents of high molecular weight are thereby administered that remain in the blood longer and cause a lesser tissue contrast. An additional problem that particularly occurs given a selective presentation of arteries or veins, is then moved into the foreground by the use of such contrast agents. If a contrast agent is added to the bloodstream for an imaging of the arteries, the veins in the examined region also additionally contrasted given a longer scan duration. In angiography, for the image data for every shown vessel, it must retroactively be decided whether it is an artery or vein, so the evaluation of the acquired image data is made significantly more difficult and a considerable time cost is incurred. This problem particularly occurs in pelvic/leg angiography on the lower leg, since here the vessels are relatively small and veins and arteries run in parallel. A high spatial resolution (therefore also a long scan duration) is thus required due to the size of the vessels; but a differentiation of arteries and veins is hampered since an artery is accompanied by two veins. Since it is not possible to establish the arrival of the venous contrasting in conventional magnetic resonance systems, the magnetic resonance data sets that are used for reconstruction of image data are normally data sets from the arterial phase and the venous phase. The reconstructed image data consequently depict both arteries and veins and a manual differentiation is necessary, which is difficult to conduct, in particular in the case of pelvic/leg angiography.

SUMMARY OF THE INVENTION

An object of the present invention is to provide a method and a magnetic resonance system to acquire angiographic data sets that enable the arrival of the venous contrasting to be determined.

According to a first aspect of the invention, a method is provided for acquisition of angiographic data sets of a region of an examination subject to be examined into whose bloodstream a contrast agent has been introduced. The method according to the invention includes the following steps. A data set of the region to be examined is acquired during a first propagation phase of the contrast agent in the bloodstream as a reference data set to determine reference data. Additional data sets of the region to be examined are then acquired. A determination is then made, based on the reference data, of variations that are caused in at least some of the additional data sets due to the arrival of a second propagation phase of the contrast agent. An identification is then made of the arrival of the second propagation phase of the contrast agent in the bloodstream, based on the determined variations The data sets preferably are magnetic resonance data set the data sets may also be computed tomography data sets. For example, magnetic resonance data sets can be acquired in an apparatus that implements a pulse sequence of slice selection gradients, phase coding gradients and frequency coding gradients, and that acquires (detects) the resulting magnetic resonance signals with an induction coil. The introduction of the contrast agent can ensue by injection, for example, with the examination subject being a person. The contrast agent can also be introduced by means of an infusion pump, for example into an arm vein. In this example, the contrast agent bolus initially passes through the heart, the lungs and the heart again, after which it arrives via the arteries into the lower legs of the examined person, that are located at least in part in the region to be examined. For example, the contrast agent initially flows through the arteries in the region to be examined. The first propagation phase of the contrast agent thus can be an arterial phase of a contrast agent enhancement (enrichment). A first MR data set that serves as a reference data set is acquired during this propagation. Furthermore, additional MR data sets are acquired in optimally short time periods, wherein a second propagation phase of the contrast agent in the bloodstream can arrive during the acquisition. The second propagation phase of the contrast agent is, for example, a venous phase of a propagation of the contrast agent. After a certain time, the contrast agent has flowed through the arteries and arrives via arterioles and venules into veins of the examination subject that are located in the region to be examined. The first propagation phase and second propagation phase of the contrast agent in the bloodstream normally apply to the region to be examined, thus do not pertain to the propagation in the arm veins directly after the introduction of the contrast agent, for example. Contrast agents are normally designed in order to cause particularly high or particularly low magnetic resonance signals in predetermined imaging sequences. The arrival of the second propagation phase of the contrast agent is therefore normally accompanied by a signal change, and thus a change in the acquired MR data sets. For example, reference data are then used for an evaluation or processing of the acquired data sets in order to establish such variations. The determination of variations advantageously ensues during the acquisition of the additional data sets. If a variation in the acquired data sets is established, the arrival of the second propagation phase can thereby be determined. For example, the point in time of the arrival of the second propagation phase or the data set in which the variation first occurred can be determined. For example, the magnetic resonance data set can be identified by a time stamp or a reference number. For example, a predetermined imaging sequence for additional acquisition of data sets can be started after the arrival of the second propagation phase was determined. The information about the arrival of the second propagation phase can also be used for an evaluation of the acquired data sets. An image reconstruction advantageously ensues from the data sets by excluding the data sets that were acquired after the arrival of the second propagation phase. Furthermore, the method is advantageously implemented automatically.

Such a method for acquisition of angiographic data sets has a number of advantages. First, the method can be implemented without manual intervention of a user, which leads to a time savings. Furthermore, with the method it is possible to determine the arrival of the second propagation phase of the contrast agent. An image reconstruction can thereby ensue in a targeted manner using only the data sets that were acquired during the first propagation phase of the contrast agent. For example, an image reconstruction can be implemented from the magnetic resonance data sets to generate an arteriograph. Data sets that were acquired during the second propagation phase (for example the venous phase) are then not taken into account, and thus are only shown in the reconstructed image data. It is thus no longer necessary to manually differentiate between arteries and veins in the image data. Such an automatic determination of the arrival of the second propagation also possesses the advantage that an incorrect association of data sets with the first or second propagation phase is avoided. For example, the times for a propagation of the contrast agent in the different phases for different examined persons can deviate significantly from one another depending on the circulatory situation, and thus an automatic determination of the arrival of the second propagation phase is particularly advantageous.

According to a further aspect of the invention, an imaging sequence that is configured to highlight contrast agent-exhibiting vessels is used to acquire the data sets. Contrast agent-exhibiting vessels are vessels that direct blood that possesses contrast agent. The contrast agent-exhibiting blood (and therefore the internal volume of the vessels) is thus normally shown with such an imaging. Various contrast agents for contrasting blood and corresponding imaging sequences that are suitable to highlight the contrasted blood are known to a man skilled in the art, and these should therefore not be discussed further here. For example, the contrast agent-exhibiting vessels can be highlighted by the intensity or amplitude of the magnetic resonance signals that are acquired from the contrast agent-exhibiting vessel differing from the magnetic resonance signals of the surrounding tissue. The contrast agent can either amplify or attenuate the magnetic resonance signals. In particular, such an attenuation or amplification depends on the selected magnetic resonance sequence, for example on the repetition times in a spin echo sequence. The use of such a sequence has the advantage that the vessels (for example arteries or veins) that contain contrast agent-enhanced blood can easily be differentiated from surrounding tissue. To acquire the reference data set, a slice is acquired with a time resolution that is greater than the time resolution that is used for the acquisition of the additional MR data sets. This is advantageous since the reference data set is evaluated to determine the reference data and a high quality of the reference data is desirable. A "slice" is a portion of a 3D magnetic resonance data set that was acquired, for example by the application of a predetermined slice-selection gradient. Magnetic resonance signals that were acquired during the application of a slice-selection gradient are then evaluated to determine the reference data.

The acquisition of the reference data set advantageously comprises the acquisition of data from a slice in the upper half of a lower leg of the examination subject. Arteries in this area, as well as veins surrounding the arteries, are easy to identify in image data, so the arrival of the second propagation phase can be reliably determined.

According to one embodiment of the invention, image data are reconstructed from the acquired data sets. Furthermore, a subtraction method is advantageously used to highlight contrast agent-exhibiting vessels in the image data. For example, a data set is acquired before the introduction of the contrast agent in the examined person, and image data are reconstructed from this data set. The image data so reconstructed can later be subtracted from the image data that were reconstructed from the data sets after introduction of the contrast agent in order to show contrast agent-carrying vessels with emphasis. An identification of the vessels in the image data is thus enabled. The reconstruction and emphasis can ensue for both the reference data set and the additional data sets.

According to another embodiment of the invention, contrast agent-exhibiting vessels are detected in image data that were reconstructed from the reference data set. For example, the detection can ensue via location of pixels with predetermined contrast relative to surrounding pixels in at least one slice image. For example, the points with a predetermined brightness (for example the brightest points) that correspond to the arteries are identified in at least one axial slice (preferably in the lower leg) in an imaging sequence that brightly depicts contrast agent-carrying arteries. However, the pixels that correspond to contrast agent-exhibiting vessels can also be presented darker than surrounding pixels, or in a different color or the like. An observation region is established around each detected contrast agent-exhibiting vessel. The observation region is advantageously circular, with a radius in a range between 0.3 cm and half the distance between the vessel that surrounds the observation region and the nearest detected contrast agent-exhibiting vessel. Such a determination of an observation region is particularly advantageous in the generation of MR angiographs of a lower extremity of an examined person since an artery in these extremities is respectively accompanied by a vein or a vein pair. A variation of the image data in observation regions of such a design can thus be expected upon arrival of the second propagation phase of the contrast agent, for example the propagation in the veins. It is particularly advantageous when the observation region does not comprise the vessel around which the observation region was established. For example, if arteries are pervaded by the contrast agent during the first propagation phase and thus are shown as bright image points in the image data, no bright image data points are presented in the observation regions of such a design. An arrival of the second propagation phase of the contrast agent can thus be detected via an occurrence of image data points with predetermined brightness.

According to another embodiment, the determination of variations comprises a checking of the observation region for image data points that depict a contrast agent-exhibiting vessel in image data that were reconstructed from the acquired additional data sets. For example, if one observation region is established in a specific slice image with the aid of the reference data set and a corresponding observation region is established in a corresponding slice image from the additional MR data sets, the occurrence of additional bright points that, for example, depict contrast agent-pervaded veins is checked. In an embodiment, image data points that depict contrast agent-exhibiting vessels are identified by their signal intensity being at or below a predetermined threshold. The signal intensity can correspond to a brightness of an image data point. Depending on the contrast agent used, the magnetic resonance sequence used and the image reconstruction methods, the image data points that depict contrast agent-carrying vessels are shown differently. By using the reference data set it can be established with which brightness such vessels are shown, for example. For example, the pixels in the observation regions that exhibit a predetermined brightness can be identified to determine variations in the data sets.

According to another embodiment, image data points from the observation region of the additional data sets that depict contrast agent-exhibiting vessels are identified via a comparison with corresponding image data points from the observation region of the reference data set. Changes of image data in observation regions can be determined simply in this way. Upon arrival of the second propagation phase of the contrast agent, for example, bright points that represent an imaging of contrast agent-pervaded veins occur in an observation region of the additional magnetic resonance data sets, for example. These can easily be identified by a comparison with a corresponding observation region of the reference data set.

The arrival of the second propagation phase of the contrast agent in the bloodstream is advantageously determined in that image data points that depict contrast agent-exhibiting vessels are located in at least one observation region upon inspection. As soon as the arterial propagation phase transitions to the venous propagation phase of the contrast agent in the region to be examined, for example, blood is depicted in the veins which exhibit contrast agent. Since the veins normally run in proximity to the arteries, the imaging in the observation regions ensues around the arteries. If such a depiction is found in the observation region, it can be assumed that the second phase of the propagation of the contrast agent has begun. For example, if additional bright points occur in the defined observation regions, this is the start of the venous contrasting. Such an identification of the start of the second propagation phase of the contrast agent is advantageous since it can ensue automatically and enables an evaluation of the data sets that were acquired before the arrival of the second propagation phase. It is also possible that a venous contrasting has already occurred in other body regions (for example in the arm veins into which contrast agent was introduced). However, such a contrasting in remote regions is insignificant since this does not impair the evaluation of the acquired data sets. The time period that is available for an acquisition of data sets before an occurrence of the venous contrasting can be optimally utilized with the described embodiment of the invention.

According to an additional embodiment of the invention, the determination of variations is made by a comparison of data points of the reference data set with data points of the additional data sets in k-space. The discovery of variations in the comparison can then represent the arrival of the second propagation phase. K-space is essentially the reciprocal space of the space in which the image data are presented. The image data can be obtained from the data points in k-space with the aid of a Fourier transformation. The filling of k-space with data points via acquisition of magnetic resonance signals with the aid of phase coding gradients and frequency coding gradients is a method known to the man skilled in the art that should not be discussed further here. MR data sets can likewise be acquired in three dimensions via application of an additional phase coding gradient. For example, if a magnetic resonance method is applied in which structures filled with contrast agent exhibit a high contrast relative to surrounding tissue, k-space thus comprises data points that are significantly based on these structures. The data points in k-space can be determined as reference data from the reference data set. These reference data can later be used in order to establish variations in additional acquired magnetic resonance data sets. The determination of variations in the data sets advantageously comprises a detection of a shift of data points with maximum or minimum intensity in k-space, wherein the start of the shift determines the arrival of the second propagation phase of the contrast agent. The arrival of the second propagation phase of the contrast agent generally results in the occurrence of additional signal sources in acquired magnetic resonance data sets. For example, maxima in k-space can shift toward higher spatial frequencies due to these structures situated closer to one another. For example, the shift can ensue via a comparison of the data points in k-space from the MR data sets with the reference data. During the first propagation phase of the contrast agent, the maximum data points in k-space from the reference data set essentially correspond to the maximum data points from the additional acquired magnetic resonance data sets. Upon arrival of the second propagation phase, a shift of the data points can ensue in k-space, using which the arrival of the second propagation phase is determined. An advantage of this embodiment is that no reconstruction of the image data is required. Since the shift can be automatically established at higher spatial frequencies, the arrival of a venous contrasting can likewise be automatically established, for example, whereby the generation of an arteriograph is enabled.

According to a further embodiment, a movement correction is applied that corrects the observation region for a movement of the examination subject. A movement of an examined person during the acquisition of data sets has the consequence that the image of a contrast agent-pervaded artery shifts in the image data of successive data sets. Such a shift can cause an occurrence of bright image data points in observation regions that were placed around the arteries, which can be incorrectly interpreted as an arrival of the second propagation phase of the contrast agent. Therefore, it is advantageous to correct the observation region corresponding to the movement of the examination subject. The observation region is advantageously corrected such that it again surrounds the imaged, contrast agent-exhibiting vessel. A reliable determination of the beginning of the second propagation phase is thus ensued even given a moving examination subject.

Furthermore, a magnetic resonance system is provided for acquisition of angiographic magnetic resonance data sets of a region of an examination subject to be examined in whose bloodstream a contrast agent has been introduced, wherein the magnetic resonance system possesses: an acquisition unit that acquires MR data sets from the region to be examined; a control unit that controls the acquisition of MR data sets such that an MR data set of the region to be examined is acquired as a reference data set during a first propagation phase of the contrast agent in the bloodstream, and the additional MR data sets of the region to be examined are acquired; and a computer that is designed such that it executes the following steps: determination of reference data from the reference data set; determination, on the basis of the reference data, of variations that are caused in at least some of the additional MR data sets due to an arrival of a second propagation phase of the contrast agent; and determination of the arrival of the second propagation phase of the contrast agent in the bloodstream on the basis of the determined variations. The computer advantageously implements these steps automatically. Such a magnetic resonance system enables the arrival of the second propagation phase to be automatically determined. This enables a reconstruction of image data to be implemented based on the magnetic resonance data sets that were acquired during the first propagation phase. The magnetic resonance system can furthermore be designed to implement one of the methods described above.

A computer-readable medium encoded with programming instructions is provided that causes the method embodiments described above to be executed in a computer system. For example, the programmed instructions can be executed by a computer system of a magnetic resonance system, with the

BRIEF DESCRIPTION OF THE DRAWINGS

FIG. 2 schematically illustrates a region of an examination subject to be examined that exhibits vessels in the form of veins and arteries, as well as schematically showing slice images during first and second propagation phases of contrast agent in the bloodstream of the examination subject.

FIG. 4 schematically illustrates the location of variations in image data from acquired angiographic magnetic resonance data sets upon arrival of a second propagation phase of the contrast agent.

FIG. 5 is a flowchart diagram of an additional embodiment of the method for acquisition of angiographic magnetic resonance data sets.

DESCRIPTION OF THE PREFERRED EMBODIMENTS

Figure 1:
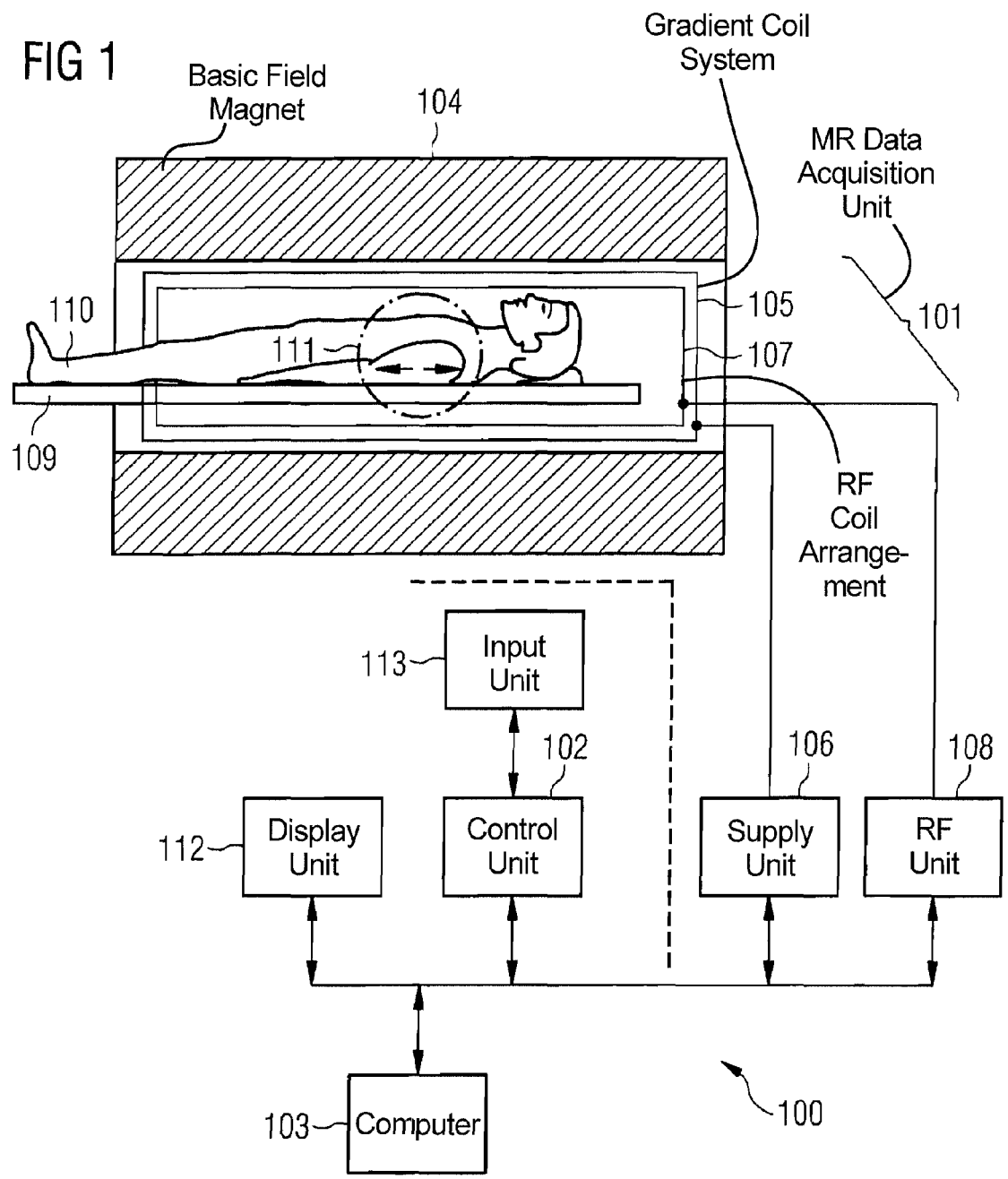
FIG. 1 schematically illustrates an embodiment of a magnetic resonance system according to the invention for acquisition of angiographic magnetic resonance data sets.

FIG. 1 schematically shows a magnetic resonance system 100. The magnetic resonance system 100 has an MR acquisition unit 101 to acquire magnetic resonance signals (magnetic resonance data sets) as well as a control unit 102 and a computer 103. The acquisition unit 101 has the components that are necessary to acquire magnetic resonance signals. Among these are, for example, a basic field magnet 104 that generates a polarization field $B_0$, a gradient coil system 105 and a supply unit 106 to generate and apply magnetic field gradients, for example a slice selection gradient, a phase coding gradient or a frequency coding gradient that are used for an imaging and spatial coding, as well as a radio-frequency (RF) coil arrangement 107 to radiate RF pulses and an induction coil to acquire magnetic resonance signals. Furthermore, the magnetic resonance system can possess a movable examination table 109 on which, for example, an examined person 110 is placed to traverse the magnet 104 of the magnetic resonance system (indicated by arrows). For example, to acquire magnetic resonance signals from a region 111 of the examined person, a magnetic field ($B_0$ field) is applied with a field coil of the magnet, on which magnetic field ($B_0$ field) is impressed a gradient in an axial (z) direction. Nuclear spins polarized by the $B_0$ field in a predetermined slice in which a predetermined magnetic field strength predominates can be excited via radiation of an RF pulse with predetermined frequency that can be controlled by an RF unit 108. Processing nuclear spins in this excited slice can be phase coded via temporally limited application of a second magnetic field gradient in the transverse direction (for example the y-direction). The decay of the excitation of the nuclear spins can be acquired as a magnetic resonance signal with the use of an induction coil (for example the RF coil arrangement 107) while a third gradient is applied in a transverse direction perpendicular to the second gradient. Special coils can also be used for this that are placed in proximity to the region of the examination subject to be examined. A two-dimensional data set that can be converted into an image data set via Fourier transformation can be acquired in k-space via application of various phase coding gradients. By the application of multiple such two-dimensional data sets in various slice-selection gradients, or by the use of an additional phase coding gradient, a three-dimensional data set of the region to be examined can be acquired. Both slice images and three-dimensional image data can be reconstructed from such a three-dimensional data set. The magnetic resonance system 100 can furthermore comprise the components that are provided in conventional magnetic resonance systems, for example a display unit 112, an input unit 113 and the like. The general functionality of an MR system is known to those skilled in the art, such that a detailed description of the general components is not necessary herein. Various sequence protocols for imaging sequences (for example a spin echo sequence) can be selected via the input unit 113, via which additional imaging parameters can also be input.

The manner of operation of the acquisition, control and computer unit of the magnetic resonance system 100 is now described with reference to FIG. 2. FIG. 2 shows a region 201 of an examination subject to be examined, in this case the lower leg of an examined person that exhibits arteries 202 and veins 203. The arteries 202 and the veins 203 are vessels of the bloodstream of the examination subject. The region 210 to be examined is placed in the field of view of the magnetic resonance system 100. The control unit 102 can now induce the acquisition unit 101 to acquire a magnetic resonance data set of the region 201 to be examined, from which magnetic resonance data set the computer 103 subsequently reconstructs image data, for example slice images or a three-dimensional representation. For the use of a subtraction method, this acquisition can ensue before an introduction of contrast agent into the bloodstream. A contrast agent is subsequently introduced into the bloodstream of the examined person. The contrast agent can be introduced into an arm vein with an infusion pump and then enters into the region 201 after passing through lungs and heart via arteries. For example, this can take 20-30 s. During a first propagation phase, the contrast agent propagates in the artery 202; it passes through arteries, capillaries and arterioles, for example. The control unit 102 initiates the acquisition of a magnetic resonance data set by the acquisition unit 101 during this propagation phase. A slice that, for example, essentially corresponds to the indicated section line 204 is thereby advantageously acquired with higher temporal resolution than the overall volume. This slice is advantageously an axial slice, meaning that it is essentially perpendicular to the z-direction or perpendicular to the longitudinal direction of the region to be examined. The computer 103 can evaluate the magnetic resonance data acquired from this slice and convert them into image data 205. The image data 205 in FIG. 2 show an axial slice image that essentially represents the drawn section 204 through the region 201 to be examined. The slice image 205 can be generated via a subtraction method using the data set acquired before the introduction of the contrast agent. A magnetic resonance sequence that generates an optimally high contrast of the contrast agent-carrying vessel relative to surrounding tissue in the image data is advantageously used to acquire the magnetic resonance data. For example, contrast agents can be used that shorten the T1 or T2 relaxation times. Spin echo sequences, gradient echo sequences or other magnetic resonance sequences with corresponding repetition times can then be used in order to produce a corresponding high contrast based on such relaxation time shortening in the imaging. For example, atoms or molecules with sufficiently large magnetic moment can be used to modify the relaxation times. For example, given a T1-weighted spin echo or gradient echo sequence, an accelerated relaxation can produce an increase of the magnetic resonance signal, which results in a brighter depiction of the contrast agent-exhibiting region. Sequences such as IR-SSFP (inversion recovery steady state free precession) or IR-FLASH (inversion recovery steady stage free precession) can also be used to improve the contrast.

The image data 205 show a negative representation in which regions that produce high magnetic resonance signals are colored dark. The contrast agent-exhibiting artery 202 is correspondingly presented as a dark point 206. Due to the amplification of the contrast with the introduced contrast agent and via application of a subtraction method, no additional structures in the image data 205 are depicted in this example. Reference data can be determined from the image data 205. The control unit 102 now controls the acquisition unit 101 such that additional data sets of the essentially identical region are acquired in the shortest possible time periods and are reconstructed by the computer 103. The reconstructed image data are checked by the computer for variations using the reference data. Contrast agent-exhibiting blood flows through the arteries 202 (for example via arterioles, capillaries and venules) into the veins 203 during the acquisition of additional magnetic resonance data sets. Since the vein 203 now likewise represents a contrast agent-exhibiting vessel at this point in time, it is depicted with high contrast in slice images. For example, 30 s are available from the acquisition of the reference data set during the arterial phase until the arrival of the venous phase, in which 30 s ten data sets with a time resolution of 3 s can be acquired for reconstruction of image data in which only contrasted arteries are shown. Reference character 207 designates a slice image that corresponds to the indicated slice plane 204 after the arrival of the second propagation phase of the contrast agent, i.e. of the venous contrasting from which additional magnetic resonance data sets were reconstructed that were acquired from the examination region 201. The slice image 207 again shows the contrasted artery 206 as well as additionally an image of the contrasted vein 203 in the form of a dark point 208. Via a comparison with the image data 205 or via consideration of the reference data, the computer 203 can establish variations in the acquired magnetic resonance data sets that are caused by the arrival of the second propagation phase of the contrast agent. For example, the computer can thus establish that the image data 207 depict an additional vessel, for example via an observation of an occurrence of new points with predetermined brightness in the image data with the aid of a threshold, or via a direct comparison of the image data 205 and 207. The concentration of the contrast agent in the veins 203 will normally slowly increase, and the veins will thus be depicted with increasing contrast in the image data 207. The computer 103 now determines the arrival of the second propagation phase of the contrast agent in the bloodstream in that it determines the arrival of variations, for example as a point in time or as a reference to a data set in which the variation was first established.

The beginning of the venous contrasting is thus established with the discovery of the variation, and the control unit 102 can prompt the acquisition unit 101 to start another magnetic resonance sequence for acquisition of additional MR data sets. For example, an imaging sequence for acquisition of high-resolution image data can be started since a time limit for an acquisition of MR data sets no longer exists after arrival of the venous phase. Via the identification of the arrival of the second propagation phase of the contrast agent, the computer 103 can now evaluate magnetic resonance data sets that were acquired before the arrival of the second phase. No contrasting of the veins 203 has occurred in these data sets, such that image data that are reconstructed from these show only the arteries 202. An arteriograph of the arteries of the region 201 to be examined can thus be generated automatically and in an advantageous manner. It is not necessary to manually differentiate between shown arteries and veins. Since the arrival of the second propagation phase is automatically established, the quality of the arteriograph is not reduced by incorrect association of MR data sets that were acquired during the second propagation phase. Furthermore, unnecessary data sets that were acquired during the first phase (i.e. during the arterial enhancement of the contrast agent) are also not considered. For example, the magnetic resonance system 100 can display the reconstructed image data to a user, or can provide the reconstructed image data or the acquired MR data sets to another computer system for processing.

Figure 3:
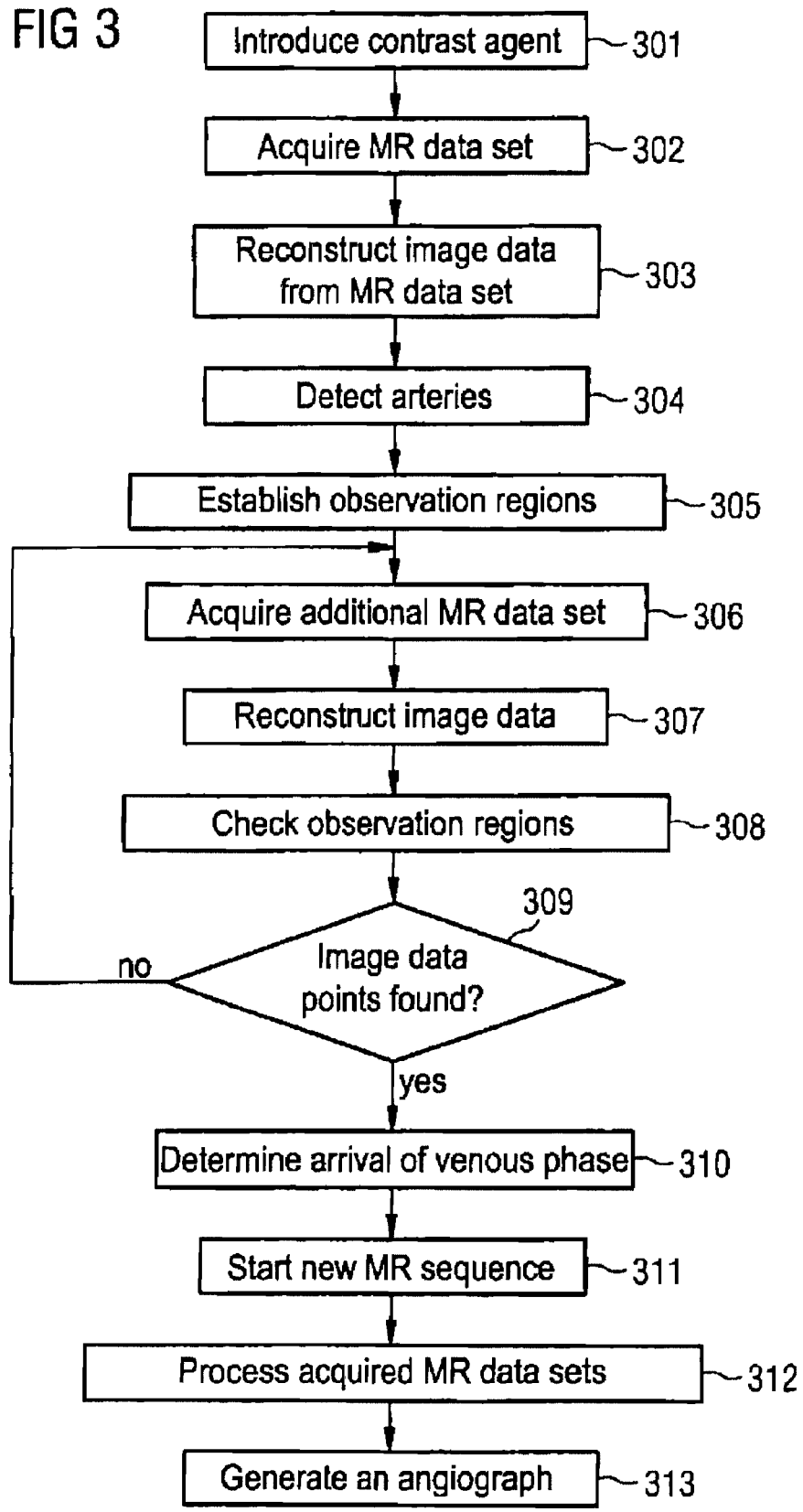
FIG. 3 is a flowchart diagram of an exemplary embodiment of the method for acquisition of angiographic magnetic resonance data sets.

FIG. 3 shows a flow diagram of an exemplary method for acquisition of angiographic magnetic resonance data sets. Before the execution of the method presented in FIG. 3, the region of the examination subject that is to be examined is positioned in the magnetic resonance system and a first data set can already be acquired, for example for a later use with a subtraction method. In a first Step 301, contrast agent is introduced into the bloodstream of the examination subject. The introduction advantageously ensues in an arm vein or at another suitable point of the bloodstream. A magnetic resonance data set is acquired in a next Step 302. As already mentioned, a magnetic resonance sequence that images contrast agent-exhibiting regions with high contrast is advantageously used for this. For example, the acquired data set can be a volume data set or only a slice data set that was acquired during a single slice-selection gradient. This data set is acquired in the arterial phase of the contrast agent enhancement. Image data are reconstructed from the acquired magnetic resonance data set in the next Step 303. The image data advantageously represent only or highlighted [sic] the contrast agent-filled vessels. The highlighting can be achieved via a subtraction method or a special MR sequence. Referring to FIG. 4, a reconstructed slice image 401 in which two contrast agent-filled arteries 402 and 403 are depicted is shown in image 4a. The representation of the image data in FIG. 4 ensues with negative contrast; however, it can also ensue with positive contrast in that regions from which greater magnetic resonance signals emanate are shown bright. Arteries are detected in a next Step 304. For example, the arteries 402 and 403 are detected in the image data 401 in that the darkest points in the image data 401 are identified. In a positive representation, the brightest points (which correspond to the arteries) can be correspondingly identified.

In a next Step 305, observation regions are established around the located arteries. As shown in FIG. 4b, a circular "region of interest" that is indicated by the dotted lines 404 and 405 is placed automatically around each identified artery 402 and 403. The observation regions 404 and 405 advantageously exhibit a radius of at least 0.3 cm and at maximum half the distance to the next artery and omit the artery itself. Observation regions established in such a manner generally exhibit no pixels that depict contrast agent-filled vessels. The observation regions 404 and 405 can possibly exhibit weak structures of surrounding tissue. However, such structures are normally presented with significantly lower contrast than the contrast agent-exhibiting vessels 402 and 403. The observation regions so established represent reference data. The observation regions are established in a slice image from a data set that was acquired as a reference data set. The reference data set is advantageously acquired directly after the arrival of the introduced contrast agent in the region to be examined.

In a next Step 306, an additional magnetic resonance data set is acquired. For example, the additional MR data set is acquired with a lower time resolution than the reference data set. In Step 307, image data are reconstructed from the additional acquired data set. The acquisition and reconstruction ensue in optimally short time periods. For example, given an acquired volume data set, slice images are reconstructed slice-by-slice via Fourier transformation.

In Step 308, the observation regions that were established as reference data in Step 305 are checked for image data points of vessels exhibiting contrast agent. After a specific time after which the contrast agent has pervaded the arteries, contrast agent-exhibiting blood has conducted back from the veins and the observations regions are checked for image data points that depict such veins or, respectively, the blood in the veins. Based on the reference data in the form of the established observation regions, the image data reconstructed from the data set are thus checked for variations that are caused by the arrival of the venous contrasting. For example, the observation regions can be checked for image data points with a predetermined brightness that corresponds to the imaging brightness of contrast agent-filled vessels. Variations can also be identified by a comparison of the image data points in the observation regions of the additional acquired magnetic resonance data set with the image data points from the observation regions of the reference data set. For example, a subtraction method can be used for a comparison. Corresponding observation regions are advantageously compared or checked in corresponding slice images.

In the decision 309 it is checked whether such image data points that depict contrast agent-filled veins were found in the observation regions. If this is not the case, it can be assumed that the second phase of the contrast agent propagation has not started, and correspondingly the acquisition of additional MR data sets is continued in Step 306. FIG. 4b shows the case in which new image data points 407 and 408 that depict contrast agent-enhanced veins occur in the observation regions 404 and 405. The occurrence of the image data points 407 and 408 can easily be established via a comparison of the observation regions 404 and 405 between the image data 401 and 406. In Step 310 the arrival of the venous phase of the contrast agent enhancement is determined via the establishment of the occurrence of the image data points 407 and 408. For example, each data set is reconstructed and checked after the acquisition, whereby the point in time at which the venous phase begins can be determined. After the arrival of the venous phase has been determined, a new magnetic resonance examination sequence is started in Step 311. Alternatively, the acquisition of additional magnetic resonance data sets can also be stopped at this point in time. The magnetic resonance data sets that were acquired before the start of the venous phase are processed in Step 312. For example, three-dimensional image data are reconstructed from the data sets in order to generate an arteriograph in Step 313. In the mentioned reconstructions of image data, subtraction methods can also be used in order to increase the contrast of the contrast agent-filled vessels to be shown. The use of the observation regions described here is advantageous since these enable a simple discovery of image data points that are caused by contrasted veins, i.e. depict the contrasted veins. An identification can also ensue using only by the observation regions, without a comparison with the image data from the reference data set, whereby the computational effort is reduced. The exemplary method enables a fast, automatic determination of the arrival of the venous propagation phase of the contrast agent.

FIG. 5 shows a flow chart of an additional exemplary embodiment of the method according to the invention. The examination subject is initially positioned in the magnetic resonance system, and a magnetic resonance signal can again be acquired before the introduction of the contrast agent. In Step 501 a contrast agent is introduced into the bloodstream of the examination subject, and the acquisition of a magnetic resonance data set that represents a reference data set ensues in Step 502. The acquisition ensues during the arterial enhancement. The magnetic resonance signals that were advantageously acquired from an axial slice of the region to be examined are analyzed in k-space. K-space contains information about the magnitude of the determined spatial frequencies regarding a reconstructed magnetic resonance image. K-space is filled with data points via acquisition of magnetic resonance signals in applied frequency coding gradients and variation of the phase coding gradients. Structures that are significantly caused by the contrast agent-exhibiting arteries are identified in k-space in Step 504. When (as described above) the contrast agent-filled arteries are imaged with high contrast relative to the background, these arteries will also significantly influence the structures present in k-space. For example, maxima and minima of the data points are identified in k-space in Step 504. The positions of these maxima or minima in k-space represent reference data. Additional magnetic resonance data sets are acquired in a next Step 505. These are analyzed as in Step 504, for example via identification of maxima and minima of the data points. A shift of maxima or minima is detected in k-space in Step 506. Variations in the magnetic resonance data sets are thus determined under consideration of the reference data determined in Step 504. For example, a shift of maxima in k-space can ensue due to the arrival of the second propagation phase of the contrast agent. If the veins are contrasted, additional structures (image data points 407 and 408) occur in the image data (as shown in FIG. 4c). The occurrence of additional, closely adjacent structures as illustrated in FIG. 4c corresponds to higher spatial frequencies in k-space. The occurrence of such structures in k-space can accordingly be detected in that it is checked whether the positions of maxima in k-space have changed. Such a variation is caused by the arrival of the venous propagation phase of the contrast agent and indicates this. In the decision 507 it is checked whether such a shift was detected. If no shift was detected, the acquisition of additional magnetic resonance data sets is continued in Step 505. If a shift was detected, the arrival of the venous propagation phase is determined in Step 508. For example, a time stamp or a reference number of the last magnetic resonance examination data set is determined for which such a shift was not yet detected. The acquired magnetic resonance data sets are processed in Step 509. It is also possible to implement the acquisition of MR data sets in Step over a predetermined time period that extends beyond the arrival of the second propagation phase, wherein the decision 507 is no longer necessary. All data sets are then processed in series in Step 506. Data sets that were acquired after the arrival of the venous phase are then retroactively identified and discarded. The data sets in which veins are thus already contrasted do not enter into a reconstruction of the image data from the MR data sets. The image data are reconstructed in the processing and an arteriograph is generated from these in Step 510. The method can again be implemented entirety automatically; a manual intervention, for example to differentiate between imaged veins and arteries, is not necessary. Moreover, in this embodiment a reconstruction of the image data during the acquisition of the magnetic resonance data sets to check for variations in the magnetic resonance data sets is not necessary, which reduces a processing time.

Furthermore, in the described embodiments it is possible to acquire magnetic resonance data sets over a predetermined time period and to subsequently check for the occurrence of variations in the magnetic resonance data sets under consideration of the reference data. For example, in the checking the data set is then established in which the second propagation phase of the contrast agent arrives. The prior data sets can then be used for a reconstruction of image data. However, in such a procedure it is possible that a number of magnetic resonance data sets is acquired in which the second propagation phase of the contrast agent has already started, and therefore are discarded, i.e. are not taken into account in a reconstruction of image data. Furthermore, the features of the various embodiments can also be combined.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring angiographic data sets of a region of an examination subject in whose bloodstream a contrast agent has been introduced, comprising the steps of:

operating an angiography apparatus to acquire an angiographic data set of a region of the examination subject to be examined during an arterial propagation phase of the contrast agent in the bloodstream, as a reference data set containing reference data;

operating said angiography apparatus to acquire additional angiographic data sets of said region;

in a processor, automatically determining based on said reference data set, variations that are caused in at least some of said additional data sets due to arrival of a venous propagation phase of said contrast agent in the bloodstream;

based on the determined variations, identifying in said processor, arrival of the venous propagation phase of the contrast agent in the bloodstream; and immediately upon determination in said processor of the arrival of the venous propagation phase of the contrast agent in the blood stream, emitting a signal from said processor that triggers execution of a predetermined diagnostic imaging sequence for acquisition of diagnostic data sets of said region of said examination subject.

2. A method as claimed in claim 1 comprising operating a magnetic resonance apparatus, as said angiography apparatus, to acquire said reference data set and said additional angiographic data sets as magnetic resonance data sets, using an imaging sequence configured to highlight contrast agent-containing vessels.

3. A method as claimed in claim 2 comprising determining said variations in said processor by computationally reconstructing image data from said magnetic resonance data sets.

4. A method as claimed in claim 3 comprising highlighting said contrast agent-containing vessels in said image data by subtraction.

5. A method as claimed in claim 3 comprising detecting said contrast agent-containing vessels in image data reconstructed from said reference data set.

6. A method as claimed in claim 5 comprising detecting said contrast agent-containing vessels in said image data reconstructed from said reference data set by identifying image points having a predetermined contrast relative to surrounding image points, in at least one slice image.

7. A method as claimed in claim 5 comprising establishing, in said image data, an observation region around each detected contrast agent-containing vessel.

8. A method as claimed in claim 7 comprising establishing each observation region as a circular observation region having a radius in a range between 0.3 cm and half of a distance between a vessel surrounded by that observation region and a nearest detected contrast agent-exhibiting vessel.

9. A method as claimed in claim 8 comprising excluding said vessel surrounded by said observation region from said observation region.

10. A method as claimed in claim 7 comprising determining said variations by analyzing said observation region for image data points that depict a contrast agent-exhibiting vessel in the image data that were reconstructed from the additional angiographic data sets.

11. A method as claimed in claim 10 comprising identifying said image data points that depict contrast agent-containing vessels as image data points exhibiting a signal intensity relative to a predetermined threshold.

12. A method as claimed in claim 10 comprising identifying image data points in the observation region in the additional angiographic data sets that depict contrast agent-exhibiting vessels by comparing image data points in the observation region with corresponding image data points in a corresponding observation region of the reference angiographic data set.

13. A method as claimed in claim 10 comprising identifying the arrival of the venous propagation phase of the contrast agent in the bloodstream by detecting image data points that depict contrast agent-exhibiting vessels in at least one of said observation regions during said analyzing.

14. A method as claimed in claim 1 comprising acquiring said reference angiographic data set and said additional angiographic data sets as magnetic resonance data sets that are respectively entered in k-space, and determining said variations by comparing data points of said reference data set in k-space with data points of respective additional data sets in k-space.

15. A method as claimed in claim 14 comprising identifying said arrival of the venous propagation phase as coinciding with a time of occurrence of said variations.

16. A method as claimed in claim 1 comprising acquiring said reference angiographic data set and said additional angiographic data sets as magnetic resonance data sets that are respectively entered into k-space, and determining said variations by detecting a shift of data points with a maximum or minimum intensity in k-space, and identifying said arrival of the venous propagation phase of said contrast agent as coinciding with a time of occurrence of said shift.

17. A method as claimed in claim 1 comprising acquiring said reference angiographic data set from a slice of the examination subject, with a temporal resolution that is greater than a temporal resolution that is used for acquisition of said additional angiographic data sets.

18. A method as claimed in claim 1 wherein the step of determining said variations comprises applying a movement correction that corrects each additional angiographic data set for movement of the examination subject during acquisition of the additional angiographic data sets, with respect to the reference data set.

19. A method as claimed in claim 18 comprising acquiring said reference angiographic data set from a slice in an upper half of a lower leg of the examination subject.

20. A method as claimed in claim 1 comprising reconstructing an arteriograph from data sets excluding data sets acquired after arrival of said venous propagation phase of said contrast agent.

21. A method as claimed in claim 1 comprising determining said variations during acquisition of said additional angiographic data sets.

22. An angiographic data acquisition system for acquiring angiographic data sets of a region of an examination subject in whose bloodstream a contrast agent has been introduced, comprising:
- an angiographic data acquisition unit that acquires an angiographic data set of a region of the examination subject to be examined during an arterial propagation phase of the contrast agent in the bloodstream, as a reference data set containing reference data;
- said angiographic data acquisition unit also acquiring additional angiographic data sets of said region;
- a processor supplied with said reference data set and said additional data sets, that based on said reference data set, determines variations that are caused in at least some of said additional data sets due to arrival of a venous propagation phase of said contrast agent in the bloodstream, and that, based on the determined variations, identifies arrival of the venous propagation phase of the contrast agent in the bloodstream and emits and output to said angiographic data acquisition unit indicating said arrival;
- said processor being configured, immediately upon determination of the arrival of the venous propagation phase of the contrast agent in the blood stream to emit a signal to said angiographic data acquisition unit; and
- said angiographic data acquisition unit, upon receipt of said signal, executing a predetermined diagnostic imaging sequence to acquire diagnostic image data sets of said region of said examination subject.

23. An angiographic data acquisition system as claimed in claim 22 wherein said angiographic data acquisition unit is a magnetic resonance data acquisition unit.

24. A non-transitory computer-readable storage medium encoded with programming instructions for acquiring angiographic data sets of a region of an examination subject in whose bloodstream a contrast agent has been introduced, said medium being loadable into a control unit of an angiography system and said programming instructions causing:
- a data acquisition unit of the angiography system to acquire an angiographic data set of a region of the examination subject to be examined during an arterial propagation phase of the contrast agent in the bloodstream, as a reference data set containing reference data, and to also acquire additional angiographic data sets of said region; and
- a processor to determine, based on said reference data set, variations that are caused in at least some of said additional data sets due to arrival of a venous propagation phase of said contrast agent in the bloodstream and, based on the determined variations, to identify arrival of the venous propagation phase of the contrast agent in the bloodstream and, immediately upon determining arrival of the venous propagation phase of the contrast agent in the bloodstream, to emit a signal to the data acquisition unit; and
- said data acquisition unit, upon receipt of said signal, to execute a predetermined diagnostic imaging sequence to acquire diagnostic image data sets of said region of said examination subject.

* * * * *